United States Patent [19]

Pomerantzeff et al.

[11] 4,213,678
[45] Jul. 22, 1980

[54] SCANNING OPHTHALMOSCOPE FOR EXAMINING THE FUNDUS OF THE EYE

[75] Inventors: Oleg Pomerantzeff, Brookline; Robert H. Webb, Charlestown, both of Mass.

[73] Assignee: Retina Foundation, Boston, Mass.

[21] Appl. No.: 837,870

[22] Filed: Sep. 29, 1977

[51] Int. Cl.² .......................... A61B 3/10; A61B 3/14
[52] U.S. Cl. .......................................... 351/7; 351/6; 351/16
[58] Field of Search ............................ 351/6, 7, 16, 13

[56] References Cited

U.S. PATENT DOCUMENTS

| | | |
|---|---|---|
| 3,417,754 | 12/1968 | Smart . |
| 3,780,979 | 12/1973 | de Guillebon .......................... 351/16 |
| 4,007,990 | 2/1977 | McDevitt et al. ..................... 351/6 X |

OTHER PUBLICATIONS

Kelly et al., "Research Study of a Fundus Tracker for Experiments in Stabilized Vision", NASA CR-1121, 9/68.

*Primary Examiner*—John K. Corbin
*Assistant Examiner*—Rodney B. Bovernick
*Attorney, Agent, or Firm*—Kenway & Jenney

[57] ABSTRACT

A scanning ophthalmoscope for repeatedly scanning a selected portion of an eye fundus has a laser source which produces a directed narrow-beam output and means for scanning the fundus with at least one selected scanning sequence. The scanning beam passes through a pivot point located in a preselected plane, preferably within the eye, for providing a wide field of view. An optical system directs light reflected from the fundus to a detector, which produces an electrical output signal proportional to the detected light. An output element provides a visual representation of the magnitude of the output signal in a spatial distribution corresponding to the scanning sequence.

14 Claims, 3 Drawing Figures

FIG. 2
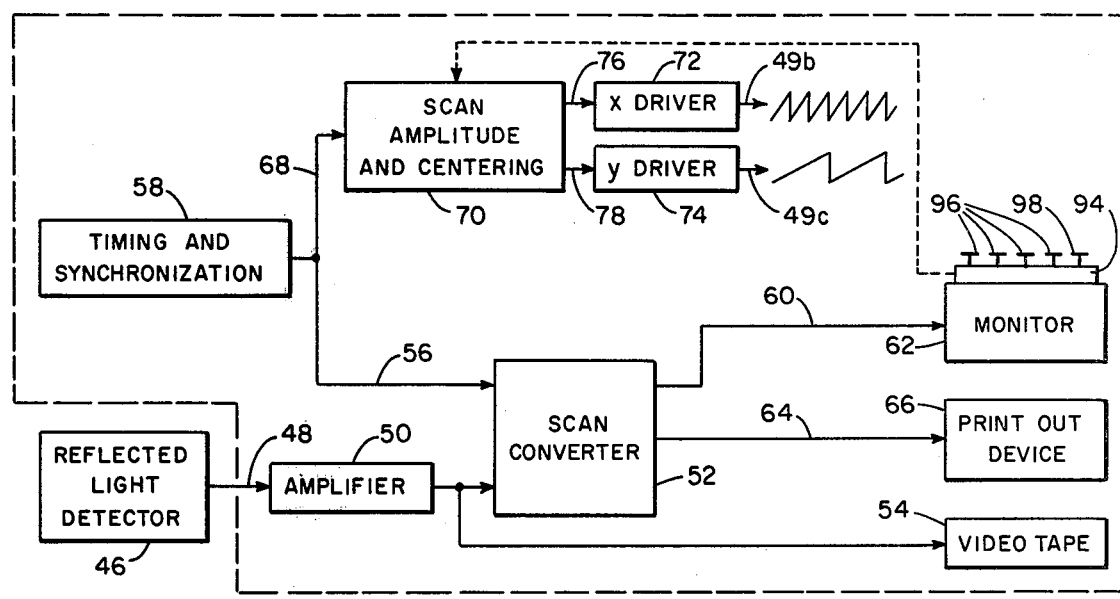
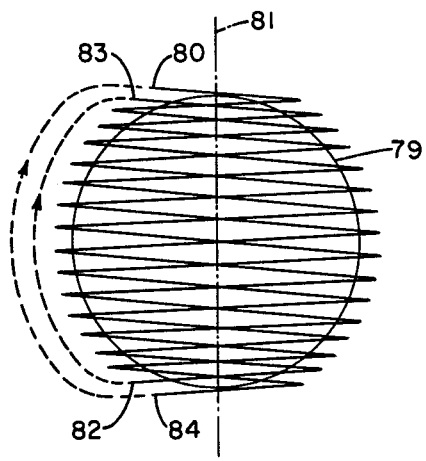
FIG. 3

SCANNING OPHTHALMOSCOPE FOR EXAMINING THE FUNDUS OF THE EYE

This invention relates generally to instruments for examining the eye and in particular to an electro-optical ophthalmoscope which provides a precise visual representative of the eye fundus on a display monitor.

BACKGROUND OF THE INVENTION

The ophthalmoscope is well known as an important aid for studying and examining the eye, and in particular, the fundus of the eye. As a result of great interest in preserving man's eyesight, ophthalmoscopes of various constructions have been built and used. Early ophthalmoscopes were mechanically manipulated so that, with an illumination source directed at the eye, the observer—using an optical system similar to a microscope—observed the fundus by manually moving the optical viewing system relative to the axis of the eye. Various constructions of more sophisticated opthalmoscopes have evolved which provide the ophthalmologist and laboratory researcher with a fine manually operated instrument for observing the retina and other layers of the fundus.

Concurrently, starting in about 1950, a number of ophthalmoscopes incorporating a television system were proposed. These "active" systems generally used the optical system of a conventional fundus camera, having a relatively small field of view, to display an image on a television screen. These systems, however, have generally been unsatisfactory because they need a large and often uncomfortable amount of illumination to overcome the low reflectivity of the fundus. Also, the systems are subject to image deterioration by high levels of stray light and scatter. The stray light appears as noise or "fog" and has caused the systems, which usually use commercial television camera components, to have low resolution and contrast. These systems do not provide the higher quality photographic images of conventional, commercially available fundus cameras, which do not need as high a light level and which provide a high resolution photograph. Thus, the "television ophthalmoscope" has not, thus far, seriously challenged either visual observation or photographic recording of the fundus.

Nevertheless, ophthalmoscopes incorporating a television system have been built. These units generally use a Zeiss or Topcon fundus camera optics for creating a first image of the fundus for TV viewing, and provide a field of view at the fundus of about 9 millimeters in diameter (or 30° of the retina). Thus, the TV camera's effective picture element, that is, the width of one picture line, extends over about 17 micrometers, i.e. 9 mm divided by 525 lines of a standard television scan, of the retina. The commercial systems are, however, subject to the above-noted significant light scattering.

As an alternative to the television systems, it has been proposed to use a cathode-ray-tube flying-spot scanning system in an ophthalmoscope, so that the illumination source is a well-defined illuminating beam. The illumination source for this device would thus be a point of light which moves across or scans the subject. A single photodetector is used to collect the reflected light. In such a system, only a single location or spot of the fundus is illuminated at any particular time, and the detector signal is derived solely from reflections due to illumination of that spot. Therefore, so long as the visual display is synchronized with the movement of the scanning spot, the visual display provides a representation of the scanned area of the fundus.

Flying spot systems, however, have generally been "light starved". That is, cathode ray tubes used as the illumination source generally lack the amount of light required to provide a good signal to noise ratio. This occurs even though the systems scan only a small field of view, for example, that photographed by the Zeiss camera. These systems, therefore, suffer from a poor signal to noise ratio because of the low contrast that results from low illumination in combination with light scatter.

Furthermore, the television systems as well as prior flying spot scanning systems have thus far not been adaptable to color imaging, because generating a color image requires more light than monochromatic imaging. Nor have they been adaptable for use with fluorescein angiography.

Principal objects of this invention are therefore to provide a scanning ophthalmoscope having improved resolution, having improved contrast, which uses a relatively low average light level, which has an improved depth of field and focus, and which can provide color imaging at high resolution.

Other objects of the invention are to provide a scanning opthalmoscope wherein image quality is independent of the regularity of the fundus structure, which operates with relatively low noise, which is safe for the subject, which is reliable, and which provides the user with great operational flexibility.

SUMMARY OF THE INVENTION

A scanning ophthalmoscope according to the invention features a laser source which produces a narrow directed light beam, and equipment for repeatedly scanning the laser beam through a pivot point lying in a plane having a selected relative location. A subject is positioned with the eye to be examined placed in such an optical alignment with the plane and with the scanning light source that the light beam scans at least a portion of the eye fundus.

The laser beam is generally deflected or varied in direction according to at least one selected scanning sequence. In particular, the scanning sequence can cover the entire fundus, or a selected portion to produce a magnified representation of that portion of the fundus. A preferred scanning sequence illuminates in both the forward and the reverse sweeps. The pattern of scanning can include a standard rectilinear television pattern or any other convenient scanning pattern including spiral and other curved or rectilinear forms.

Further in accord with the invention, the ophthalmoscope features a detecting element for providing an electrical signal proportional to the reflection from the fundus of the illumination by the scanning laser source. An output device connected to the detecting element provides a visually-perceptible output representation of the magnitude of the electrical signal in a spatial distribution corresponding to the scanning sequence. This resultant visual representation represents with fine clarity and contrast at least a portion of the eye fundus.

A preferred embodiment also features apparatus for generating primary timing signals, first and second rotatable mirrors, and apparatus responsive to the timing signals for synchronizing the extent and the rate of mirror rotation for directing the laser beam according to the selected scanning sequence. The ophthalmoscope further has apparatus responsive to the primary timing signals for synchronizing the rotation of the mirrors with the output signal from the detecting element for providing the visual output representation.

In order to provide a scanning ophthalmoscope having maximal sensitivity and minimal response to scattered light, the incident scanning light beam from the laser source has a small cross-sectional area, while the reflected beam has a relatively broad or large cross-sectional area. In this regard, the scanning beam and the reflected light are substantially coaxial for a finite span between the preselected plane and at least an optical turning region anterior of the pivot point and past which the scanning light and the reflected light are no longer coaxial. Near the turning region, where the scanning light and the reflected light are coaxial, the scanning light traverses a substantially smaller cross-sectional area than that which contains the reflected light.

While the visual display is generally a cathode ray tube or other visual display, a long-term storage medium can be used to store the resultant image. For example, the invention further features magnetic tape storage, and output printing apparatus for producing a hard copy record of the visual representation.

The preferred embodiment also features a laser having at least two energy output states to effect photocoagulation at the eye fundus.

DESCRIPTION OF THE DRAWINGS

These and other objects, features, and advantages of the invention will appear from the following description of preferred embodiments of the invention, taken together with the drawings in which:

FIG. 2 is a block diagram of electrical circuitry for the scanning ophthalmoscope of FIG. 1; and FIG. 3 is a diagram of a preferred scanning path for the embodiment of FIG. 1.

DESCRIPTION OF A PREFERRED EMBODIMENT

General Description

Figure 1:
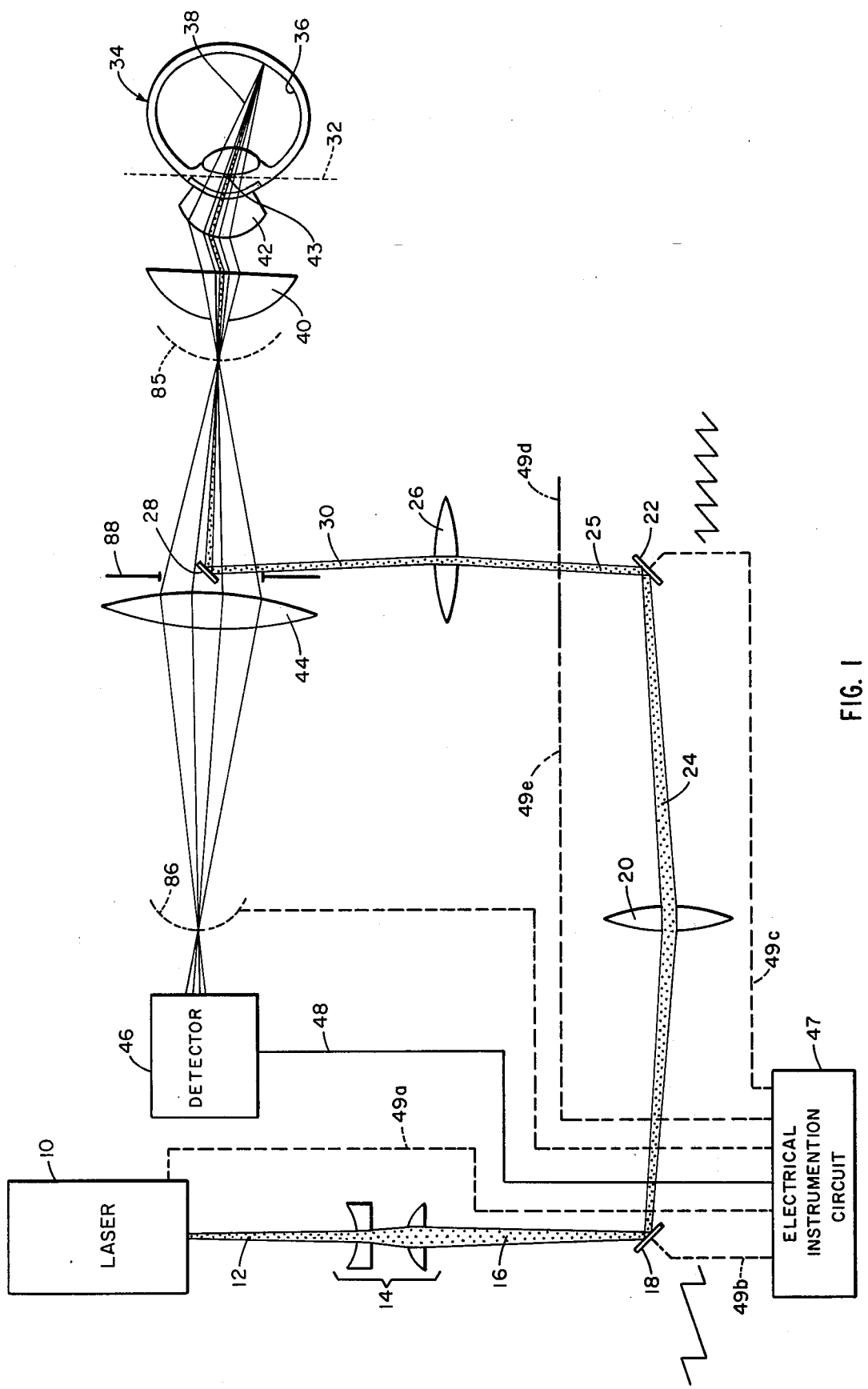
FIG. 1 is a diagrammatic representation of a scanning ophthalmoscope according to the invention and showing the optical light path from the laser source to the eye and from the eye to the detecting element.

Referring to FIG. 1, a scanning ophthalmoscope according to the invention has a laser energy illumination source 10 producing a narrow-beam, slightly diverging, highly directed light output 12. Light output 12 passes through a beam shaping optics 14 which corrects for the natural divergence of output 12 and produces a slightly converging beam 16. A deflection element repeatedly deflects or varies the direction of beam 16 according to a selected scanning sequence. The illustrated deflection element has a first light deflecting device, for example a scanning mirror 18, which directs the beam 16 toward a first transfer lens 20, and has a second light deflecting device, for example, a second scanning mirror 22. Scanning mirror 22 deflects the directed beam 24 according to the selected scanning sequence and directs the resulting beam 25 through a second transfer lens 26 and, in the illustrated embodiment, onto a positionally fixed turning mirror 28. Mirror 28 is oriented to redirect the scanning light beam 30 from the second scanning mirror 22 toward plane 32 having a selected relative location and with which the eye 34 being examined can be optically aligned.

The incident scanning light beam 30 reflected by mirror 28 enters the eye and is directed onto the eye fundus 36. The fundus reflects a portion 38 of the incident light to exit from the interior of the eye through the pupil. Lenses exterior of the eye, for example lenses 40, 42 and 44, focus the reflected light onto a detecting element 46.

The detecting element 46 is connected over a line 48 to an electrical control and monitoring circuit 47. The circuit 47 provides electrical control signals to the laser 10 over a line 49a, and provides electrical drive signals to the laser output deflection element, here scanning mirrors 18 and 22, over lines 49b and 49c respectively. The circuit 47 also applies an electrical control signal over a line 49e to a shutter mechanism 49d (described in greater detail below).

The electrical signal which the detecting element 46 applies to the electrical control and monitoring circuitry over line 48 is proportional, within the linear operating limits of the detecting element, to the intensity of the light incident on a measuring surface of the detecting element. As FIG. 2, shows, within the circuit 47 an electrical amplifier 50 receives the detector signal. The output of the amplifier 50 is applied to a scan converter 52 and, in the illustrated embodiment, to a video tape recording device 54. The scan converter also receives primary timing signals over lines 56 from a timing and synchronization circuit 58. The scan converter produces output signals representing the resultant ophthalmic image, and applies corresponding signals over lines 60 compatible with a visual display monitor 62 and over lines 64 compatible with a print-out device 66. The apparatus can also be implemented, with known equipment and techniques, to transmit signals conveying the visual display to a distant location, for example over telephone lines.

The timing and synchronization circuit 58, which includes a clock, also provides primary timing signals over lines 68 to a scan amplitude and centering control circuit 70. This circuit generates analog drive signals over lines 76 and 78 for an X-axis driver 72 and for a Y-axis driver 74. The output of the "X" driver 72 is connected over lines 49c to the X-axis scan mirror 22 and the output of the "Y" driver 74 is provided over lines 49b to drive the Y-axis scan mirror 18.

As described in more detail below, the apparatus which the invention provides produces a detector output signal with a signal to noise ratio which is comparatively high, especially when one considers the relatively high turbidity of the media within the eye through which the optical measuring energy must pass. To achieve this result, the signal degradation due to the scattering of light in traversing the eye is uniquely minimized by employing the laser light source preferably in combination with a small-aperture incident light beam, in contrast to the wide field light dispersion or wide aperture sources used in the prior art.

The Laser Source

The laser light source 10 provides energy emission at the known frequencies which yield maximum contrast to distinguish the structure of interest. Preferably, the illumination source 10 is an argon-krypton laser, from which energy is available, at at least two power levels, and at wavelengths of 488 nm., 514 nm., 531 nm., 568 nm., and 647 nm. The two shorter wavelengths are useful for examining the superficial layers of the retina; and the green wavelengths, especially 568 nm., provide high contrast demonstration of the retinal vasculature, retinal pigment epithelium changes, and the choroidal vessels in less pigmented periphery fields. The red wavelength, 647 nm., is optimal for examination of pigment masses in the choroid and the choroidal vessels in darkly pigmented fundus areas.

A monochromatic system using an individual emission wavelength is the simplest system to implement and provides the highest resolution. However, full color imaging can also be accomplished easily with the argon-krypton laser by using several (or all) of the laser emission wavelengths at once. A color display can then be generated on a single monitor, or separate monitors can display each monochromatic image making up the full color display.

The Scanning Input

In a typical system according to the invention, the laser light output 12 is shaped by beam shaping optics 14 to provide an illuminating beam that at the fundus has a narrow width or "waist" of typically about 12 micrometers in diameter. The mirrors 18 and 22 deflect the beam with a selected sequency to scan the laser illumination across the fundus area that is to be viewed. Galvanometer controls such as those manufactured by General Scanning of Watertown, Massachusetts are typical for driving and controlling the position of the mirrors. For a typical television interlaced scan (with or without the retrace or flyback time as described below), mirror 22 can employ a General Scanning type G-112 unit for the faster X-axis motion, and mirror 18 can employ a type G-0606 for the slower scanning along the Y-axis. Alternatively, a polygonal rotating mirror such as a Lincoln Laser (Phoenix, Arizona) No. PO-24 (A Grade) can be used for the "X" direction. Each FIG. 2 driver 72, 74 can be a General Scanning drive amplifier No. AX-200.

While mirrors 18 and 22 can be driven according to any of numerous scanning patterns, FIG. 3 illustrates a preferred pattern for a full fundus scan. This preferred scanning pattern resembles a conventional interlaced television scanning pattern. However, instead of having a retrace time during which the video or detected light signal is blanked or inhibited, image scanning is continued during the backward sweep, i.e. from the right hand end of the image area to the left, at the same scanning rate used in the forward direction. The result of this scanning format is that, an alternate lines of the scan, the detecting element produces an output signal that represents the fundus in a "forward" and then a "backward" orientation respectively. Thus, if circle 79 represents the full fundus field of view to be scanned, this illustrative scan begins at a top left-hand location 80, and just outside the actual field of interest. As the Y-axis mirror 18 progressively sweeps the beam to move downward in FIG. 3, the X-axis mirror 22 sweeps the beam horizontally back and forth, i.e. from side to side. For this operation, the "X" scan mirror, corresponding to the horizontal deflection direction in FIG. 3, is driven, for example, with an electrical signal having a waveform which has an average value corresponding to a central vertical axis 81 about which the mirror is deflected.

As the end of the first scan of the fundus field 79, corresponding to a beam position 82 in the lower left-hand quadrant outside of the field 79 of interest, the Y-axis driver is reset to the beginning of the scan but is vertically offset from location 80 to location 83 to provide a second scan interlaced with the first one. At the termination of the second scan, corresponding to beam position 84, the Y-axis driver is reset to position 80 and the next scan, the third scan is executed along the same path as the first scan.

FIG. 3 shows that the illustrated "X" or horizontal scan extent is not constant but varies according to the field being examined. It is also acceptable to provide an "X" scan of constant extent, the effect being to simplify the electrical circuitry while increasing the length of the scan path and hence the linear scan rate. In either case, the total time required for scanning the image can be reduced, compared to conventional scanning techniques incorporating a flyback or retrace time during which scanning does not occur, and the instrumentation for controlling mirrors 18 and 22 is simplified by allowing the use of sinusoidal waveforms to drive the mirrors. Other image scanning patterns, such as a standard television interlaced scan having retrace time, can be used.

As stated, the input scanning beam is imaged on and scans across the fundus of the eye. However, to provide wide-angle fundus illumination, transfer lenses 20 and 26 (FIG. 1) in combination with imaging lens 40, wide angle lens 42, and turning mirror 28 provide a pivot point 43 for the scanning beam at the plate 32, which is preferably located at the pupil of the eye. Turning mirror 28 is therefore positioned in alignment with an image of the pupil. With this arrangement, the wide angle lens 42, which is similar, for example, to the contact lens described in U.S. Application. Ser. No. 292,150, filed Sept. 25, 1972, in combination with the illustrated laser optical system enables a scanning field at the fundus of the eye of about 150° to be achieved.

Reflected Light System

Light is reflected from the fundus 36 of the eye in all directions. The incident scanning illumination which reflects directly through the pupil forms the reflected light signal which it is desired to detect. In addition, there is also unwanted intra-eye scatter, i.e. incident light which reflects from the turbid media within the eye. The resulting unwanted scattered light signal, and that incident light scattered from the corneal surface of the eye and external lens elements constitute an undesired noise signal in the ophthalmic system. This scattering light signal, if detected by element 46 (FIG. 1), degrades the signal to noise ratio of the system and reduces the contrast and resolution of the system.

However, the unwanted scattered light signal is significantly reduced, according to the invention, by structuring the system to employ and take advantage of the narrow-beam dimensions of the novel laser scanning beam, and by providing a reflected-light collection system which has a large aperture, i.e. a large collection area, for information-bearing reflected light. The collection area is preferably located at and limited to known areas at which light reflected directly from the illuminated point or spot on the fundus is dominant. Thus, while the scanning illumination incident on the fundus 36 is reflected and scattered in all directions, substantially only that light reflected directly from the illuminated fundus point, and exiting directly through the pupil of the eye, is directed towards the detecting element.

To attain this operation, lenses 40 and 42 form a first image of the fundus at a location 85 anterior of the eye and these lenses. Lens 44 projects this image toward the detecting element 46 and forms a second image at a second anterior location 86 immediately forward of the detecting element 46. The image formed at location 86 generally has a diminished spatial resolution due to use of a large collection aperture of lens system 40, 42. A scanning detector having a low spatial resolution detecting surface can be used as the detecting element as described below.

While it is desired to collect all of the light energy reflected by the illuminated fundus point, in the preferred embodiment illustrated, the optical paths of the incident and of the desired reflected light rays are coaxial between the fundus being scanned and the turning mirror 28. Consequently, mirror 28 blocks a central portion of the reflected light which otherwise would be detected.

As noted above, unwanted light scatter has at least two sources, intra-eye scatter and scatter at the exterior surfaces of the eye. To reduce the scattering of reflected light at the exterior surfaces of the eye, a stop 88 is placed in the plane of the pupilary image (at turning mirror 28). The stop has an aperture which corresponds in size to the image of the pupil of the eye at this plane. Typically, the locations of lens 44 and of stop 88 are dictated by the choices of lenses 40 and 42.

The illustrated scanning system is also provided with an automatic shutter to prevent inadvertent exposure of the eye to the laser output, for example when the mirrors are stationary and thus to reduce possible discomfort. For this purpose, a shutter mechanism 49d is interposed in the optical path between the laser 10 and the eye. The illustrated shutter, located between the mirror 22 and lens 26, employs an opaque screen attached to a rotary solenoid. In the de-energized state, the solenoid positions the opaque screen in the optical path between the laser and the eye. Upon being energized, typically in response to the scanning movement of the mirrors 18 and 22, the solenoid pivots the optical screen out of the optical path.

The Light Detection Means

With further reference to FIG. 1, the detecting element 46 can employ either of at least two detecting systems. Each system converts the incident light signals to electrical signals, and has different advantages and disadvantages. The simplest system uses a photomultiplier tube (PMT), such as an RCA Type 4526 or a United Detection Technology Type PIN-020A. The photosensitive surface of the photomultiplier tube is optically aligned with the reflected light which lenses 40, 42 and 44 project, and is positioned at a plane typically corresponding to an image of the pupil of the eye so that the illumination region imaged on its sensitive surface is stationary. Techniques for implementing this detection system are well known in the art.

In a second detection system, a low-spatial resolution energy detection device, such as Hammatsu Type R-571 manufactured in Japan, is aligned with the secondary image 86 of the fundus. With this low resolution detector, only that portion of the detection system corresponding to the vicinity of the fundus surface being illuminated is responsive to incident light; all other portions of the detection surface are insensitive. With this arrangement, light scattered from the nonilluminated portions of the eye and which passes through the collecting lens system does not contribute to the output of the detection device unless it falls upon the light sensitive portion of the detector. As a result, the noise due to unwanted scattered light is significantly reduced. This system is more complex than the PMT system and, in effect, the detector is scanned synchronously with the fundus.

Description of the Electrical Circuitry

Referring now to the electrical circuit portion of the ophthalmoscope scanning system (FIG. 2), the illustrated system is designed to operate at a scan rate of 3 complete (6 interlaced) frames per second. The clock rates and timing required to achieve this scan rate are well known in the art and are provided by the timing and synchronization circuit 58. The clock and timing signals are applied to the scan amplitude and centering circuit 70 over line 68. Circuit 70 uses the clock signals to generate, depending upon the size and location of the scanning sequence, the signals required by the X and Y drivers to drive the rotating mirrors.

The illustrated circuit 70 includes a "zoom" capability to provide the flexibility of more closely examining (magnifying) a small portion of the fundus. The effect is to magnify or enlarge the relatively smaller portion (smaller than a full fundus scan) of the fundus for either visual examination on a monitor or for storage, the enlarged presentation providing more detail than the "full scan". In those instances where the resolution of the laser scanning illumination at the surface of the fundus is sufficiently great, that is, if the ratio of the "waist" or diameter of the scanning illumination at the fundus to the extent of the scan is less than about 1:1000, the detailed structure may be enhanced.

The "zoom" capability is controlled by circuitry within the scan amplitude and control circuit 70 which receives data defining the extent of the scan from a control panel 94, typically associated with monitor 62. Control panel 94 has a plurality of knobs 96. The size and location of the fundus scan are determined by analog signals derived from the position of the panel knobs 96. In the illustrated embodiment a change in the scan size does not change the size of the display on the monitor 62. Thus, for example the lower lefthand quadrant of the fundus can be scanned and displayed on the monitor at a magnification of approximately twice the normal monitor viewing size (of the full fundus display). The circuitry 70 for receiving and interpreting the signals from panel 94 as knobs 96 are turned, thereby changing the extent of the scanning illumination, is well known in the art. Digital circuitry can also be used.

In combination with the panel knobs described above, display monitor 62 can also incorporate a cursor, whose position is controlled by knobs 96, to designate, for example, the center of the desired field of view. In a preferred embodiment the cursor is set to the center of the desired scan and a single "zoom" control knob determines the extent of the scan or field of view.

The ophthalmoscope of the present invention can also effect photocoagulation of the fundus. The cursor is placed, preferably using a magnified image, at the precise location where photocoagulation is to take place. A switch 98, at monitor 62 is then depressed and, in response, the scan amplitude and control circuit 70 provides a high energy output signal level to laser 10 over line 49a at the precise time when the scanning laser beam is at the fundus location corresponding to the position of the cursor. The laser high energy output is sufficient to effect photocoagulation at that position over the course of a number of frames.

In a typical operation, the system is turned on and a patient is positioned so that his eye is in contact with contact lens 42. Typically, the subject's eye will then be optically aligned with the scanning laser beam and with the preselected plane 32 so that the laser is focused on the fundus of the eye. Initially, the full fundus is scanned and the visual representation on monitor 62 displays the full fundus area, preferably in a monochromatic display although a color display as noted above can be used. The optical system is adjusted, if necessary, for optimum focus during this initial stage.

The illustrated system is designed to complete the scan of the selected fundus area six times per second. The reflected light is detected, and the resultant signal amplified and delivered to the scan converter 52. The converter also receives the clock and timing signals from circuit 58 necessary to decode the detector output. The scan converter stores the detector data and develops, at its output to line 60, an output signal representing a standard interlaced display monitor signal, repeating at sixty times per second (the desired monitor repetition rate). (A typical scan converter 52 is the Model PEP-500, manufactured by Princeton Electronic Products of Princeton, N.J. A typical monitor 62 is the Sierra Scientific Model No. HD-1501.) This signal from the scan converter drives the monitor 62 to display a flicker-free image on a standard monitor, although the fundus is scanned at only six times per second.

After the operator examines the full fundus scan, s/he can change the instrument field of view effectively to provide magnification of the field. The operator controls the center and extent of the field of view through panel 94, or through the panel 94 in combination with a display cursor, which defines the center of the magnified scan. The scan amplitude and centering circuit 70 responds to the signals from panel 94 and directs the scan to the selected fundus area. That selected area is scanned at the same rate, six times per second, and is displayed on the full monitor screen. Hence, if the fundus size is within the limits noted above, a significant increase in viewing resolution is available. Thereafter, using the monitor keyboard controls, a full fundus scan or any other fundus area can be displayed. Up to 7× magnification is typically available.

Other embodiments of the invention including additions, subtractions, deletions, or modifications of the disclosed embodiment will be obvious to those skilled in the art and are within the scope of the following claims.

What is claimed is:

1. A scanning ophthalmoscope for providing a visual representation of an eye fundus under scanned illumination, said ophthalmoscope having the improvement comprising
   A. scanning laser source means for projecting a fundus-illuminating laser beam which scans according to a selected scanning sequence,
   B. optical means
      for directing said scanning laser beam through a pivot point in a plane having a location selected relative to the laser beam for receiving the pupil of the eye being examined for introducing the scanning laser beam into an eye so located through a small portion only of the eye pupil, and
      for directing said scanning beam to travel from said pivot point onto a wide-angle region of the fundus of the eye located with the eye pupil at said selected plane,
   C. optical detecting means for receiving light reflected from the eye fundus in response to illumination with said scanning beam, said detecting means being arranged for receiving light which traverses from within the eye through at least a major portion of the eye pupil, and for producing an electrical signal in response to the received light and with correspondence to said scanning sequence, and
   D. output means for providing a fundus-imaging output representation in response to said electrical signal.

2. The scanning opthalmoscope of claim 1 p1 A. further comprising means for selecting a second scanning sequence,
   B. in which said scanning source means includes direction-varying means responsive to said selecting means for varying the direction of said light output according to said second scanning sequence, and
   C. in which said direction-varying means, when operating according to said second scanning sequence, deflects said light beam across a smaller cross-sectional area of the fundus than when the direction-varying means is responsive according to the first scanning sequence.

3. The scanning opthalmoscope of claim 1 further comprising
   A. a long term storage medium, and
   B. means for recording measured light responsive to said received light on said storage medium in a format for providing a visual representation when said measurements are retrieved.

4. The scanning opthalmoscope of claim 1 wherein said
   scanning source means comprises means for causing said light beam to scan in both forward and reverse x-axis directions.

5. The scanning opthalmoscope of claim 1 wherein said output means comprises
   a signal rate conversion means for receiving the electrical signals from the detecting means at a first slow rate and for providing electrical signals to an output display device at a second rate, different from the first rate,
   whereby a flicker-free visual representation may be generated at said display device.

6. The scanning opthalmoscope of claim 1 wherein said detecting means comprises
   a low spatial resolution energy detection device optically aligned with an image of the eye fundus for providing a photosensitive surface selectively sensitized in synchronism with the scanning beam.

7. A scanning opthalmoscope according to claim 1
   A. further comprising means for generating primary timing signals
   B. in which said scanning laser source means includes a laser source, first and second mirrors for varying the direction of light output from said source and each mounted for selected rotation, and first means responsive to said primary timing signals for synchronizing the extent and the rate of rotation of said mirrors for varying the direction of the laser light from said source to project said fundus-illuminating laser beam with said selected scanning sequence, and
   C. in which said output means includes second means responsive to said primary timing signals for synchronizing the rotation of said mirrors with the optical detecting means for providing said fundus-imaging representation.

8. A scanning ophthalmoscope according to claim 1

A. in which said optical means and said detecting means direct both said scanning laser beam and said reflected light along substantially coaxial paths between said selected plane of said pivot point and a turning region, and B. in which said optical means includes means for directing said scanning laser beam within a cross-sectional area substantially smaller than the cross-sectional area of said reflected light along the extent of said coaxial paths.

9. A scanning ophthalmoscope according to claim 8 in which said optical means further comprises a wide-angle contact lens for placement contiguous with the eye being examined and in optical alignment with said scanning laser source means, for enabling the scanning and the imaging of at least 150 degrees of the eye fundus.

10. A scanning ophthalmoscope according to claim 1 having the further improvement in that said scanning laser source means includes a laser source having at least two selectable output power levels, a first of said levels having sufficient intensity only for fundus-illumination for imaging purposes and the second of said power levels having sufficient intensity to effect photocoagulation at the fundus.

11. A scanning opthalmoscope according to claim 10 having the further improvement comprising
   A. means for selecting a location of the fundus of the eye being examined for performing photocoagulation and
   B. means for initiating a brief controlled interval of laser operation at said second high-power level in response to said scanning laser beam being directed at said selected fundus location.

12. A scanning ophthalmoscope according to claim 1 having the further improvement in which said optical detecting means includes
   A. a photosensitive detection element, and
   B. means for producing said electrical signal in response to light incident on only a portion of said detection element selected synchronously with the scanning illumination of the fundus by said scanning laser beam.

13. A scanning ophthalmoscope for providing a visual representation of the eye fundus under scanned illumination comprising
   a laser source having a directed, narrow beam, light output,
   first and second galvanometer drive members for rotating first and second light reflecting mirrors respectively,
   said first and second drive members being responsive to drive signals from a first synchronizing means for synchronizing the rotation of said mirrors with each other, according to a selected scanning sequence,
   said mirrors repeatedly varying the direction of said light output according to said selected scanning sequence for providing a scanning, narrow beam, laser light source,
   a turning mirror for directing the scanning narrow beam light source in a direction toward a preselected plane,
   means for optically providing said scanning light source with a pivot point in said plane through which the scanning, narrow beam, light source passes,
   detecting means for receiving light reflected from the eye fundus and for providing an electrical signal output related to the magnitude of light reflected from the received light,
   said scanning laser source and said reflected light being substantially coaxial between the selected plane and the turning mirror, and the scanning light source traversing a substantially smaller cross-sectional area than the reflected light source in a plane normal to said lights and positioned at said turning mirror, and
   output means connected to said detecting means for providing a visual output representation of the magnitude of the electrical signal in a spatial distribution corresponding to said scanning sequence,
   whereby an eye may be placed in optical alignment with the preselected plane and with the scanning light source for providing a visual representation of at least a portion of the fundus of the eye.

14. A scanning opthalmoscope for providing a visual representation of an eye fundus under scanned illumination, said ophthalmoscope having the improvement comprising
   A. a laser source producing a directed narrow light beam.
   B. means for generating primary timing signals,
   C. means for repeatedly varying the direction of said light beam according to at least one selected scanning sequence, said direction-varying means including
      first and second mirrors mounted for rotation, and
      first means responsive to said primary timing signals for synchronizing the extent and rate of rotation of said mirrors for varying the direction of said laser light beam according to said selected scanning sequence, including first and second galvanometer drive member for rotating said first and second mirrors respectively,
   D. means in optical alignment with said laser source and with said direction-varying means for directing said scanning beam through an optical pivot point lying in a plane having a selected location,
   E. detecting means for receiving light reflected from an eye fundus in response to illumination by said scanning beam and for producing an electrical signal proportional to the magnitude of the received reflected light, and
   F. output means connected with said detecting means for providing a visually perceptible output representation of the magnitude of said electrical signal in a spatial distribution corresponding to said scanning sequence,
   said output means including second means responsive to said primary timing signals for synchronizing the rotation of said mirrors with the detecting means output signal for providing said visual output representation,
   whereby said visual representation is of the fundus of an eye which is in optical alignment with said scanning laser beam and is selectively located relative to said plane.

* * * * *

UNITED STATES PATENT AND TRADEMARK OFFICE
CERTIFICATE OF CORRECTION

PATENT NO. : 4,213,678
DATED : July 22, 1980
INVENTOR(S) : Oleg Pomerantzeff and Robert H. Webb It is certified that error appears in the above-identified patent and that said Letters Patent are hereby corrected as shown below:

Column 1, lines 7 and 8, change "representative" to --representation--.

Column 4, line 22, delete the comma "," after "FIG. 2".

Column 5, line 3, change "periphery" to --peripheral--.

Column 5, line 47, change "an" to --on--.

Column 5, line 62, change "As" to --At--.

Column 6, line 29, after "Application" delete the period ".".

Column 7, line 7, change "desired" to --desirable--.

Column 10, line 9, delete "pl", and start "A." on the next line as a sub-paragraph of claim 2.

Column 12, line 27, after "beam" delete the period " . ".

Signed and Sealed this

Eighteenth Day of May 1982

[SEAL]

Attest:

GERALD J. MOSSINGHOFF

Attesting Officer

Commissioner of Patents and Trademarks